(12) United States Patent
Lu et al.

(10) Patent No.: US 9,360,439 B2
(45) Date of Patent: Jun. 7, 2016

(54) IMAGING SYSTEM

(71) Applicant: Industrial Technology Research Institute, Hsinchu (TW)

(72) Inventors: Hui-Hsin Lu, New Taipei (TW); Jiun-Lin Guo, Hsinchu (TW); Wei-Hsin Wang, Taipei (TW); Ting-Hsuan Chen, Taoyuan County (TW); Tsung-Ter Kuo, Taichung (TW)

(73) Assignee: Industrial Technology Research Institute, Hsinchu (TW)

(*) Notice: Subject to any disclaimer, the term of this patent is extended or adjusted under 35 U.S.C. 154(b) by 287 days.

(21) Appl. No.: 14/133,669

(22) Filed: Dec. 19, 2013

(65) Prior Publication Data
US 2014/0185752 A1    Jul. 3, 2014

Related U.S. Application Data

(60) Provisional application No. 61/739,017, filed on Dec. 19, 2012.

(30) Foreign Application Priority Data

Nov. 20, 2013   (TW) .............................. 102142336 A (51) Int. Cl.
*G01N 23/04* (2006.01)
*G01N 23/087* (2006.01)
*A61B 6/00* (2006.01)

(52) U.S. Cl.
CPC ............ *G01N 23/087* (2013.01); *A61B 6/4035* (2013.01); *A61B 6/4241* (2013.01); *A61B 6/482* (2013.01); *A61B 6/484* (2013.01); *G01N 2223/423* (2013.01)

(58) Field of Classification Search
CPC ............. G01N 23/04; G01N 23/087; G01N 2223/423; A61B 6/4035; A61B 6/4241; A61B 6/484
See application file for complete search history.

(56) References Cited

U.S. PATENT DOCUMENTS

| 4,622,688 | A |   | 11/1986 | Diemer et al. |
| 4,969,175 | A | * | 11/1990 | Nelson ................. B82Y 10/00 378/146 |
| 6,526,121 | B1 |   | 2/2003  | Hwu et al. |
| 7,286,640 | B2 |   | 10/2007 | Yun et al. |
| 7,420,675 | B2 |   | 9/2008  | Giakos |
| 7,924,973 | B2 |   | 4/2011  | Kottler et al. |
| 8,184,771 | B2 |   | 5/2012  | Murakoshi et al. |

(Continued)

OTHER PUBLICATIONS

"Office Action of Taiwan Counterpart Application", issued on Oct. 21, 2015, p. 1-p. 7.

(Continued)

*Primary Examiner* — Courtney Thomas
(74) *Attorney, Agent, or Firm* — Jianq Chyun IP Office (57) ABSTRACT

An imaging system used for material discrimination of an objet is provided. The imaging system includes an X-ray source and an imaging sensor. The X-ray source generates multienergy polychromatic X-ray, wherein there is an integral-multiple relationship between the multi-energy-band of the X-ray. The object is placed between the X-ray source and the imaging sensor. The X-ray is transmitted toward and imaged by the imaging sensor through the object. An imaging multi-energy-band of the imaging sensor corresponds to the multi-energy-band of the X-ray.

12 Claims, 9 Drawing Sheets

(56) References Cited

U.S. PATENT DOCUMENTS

| | | | |
|---|---|---|---|
| 8,306,183 B2 | 11/2012 | Koehler | |
| 2003/0185344 A1* | 10/2003 | Ukita | H01J 35/08 378/143 |
| 2009/0092227 A1* | 4/2009 | David | A61B 6/4233 378/36 |
| 2012/0020461 A1 | 1/2012 | Roessl et al. | |

OTHER PUBLICATIONS

Weon et al., "Phase contrast X-ray imaging," Int. J. Nanotechnology, Jan. 2006, pp. 280-297, vol. 3.

Dicken et al, "Combined X-ray diffraction and kinetic depth effect imaging," Optics Express, Mar. 28, 2011, pp. 6406-6413, vol. 19, No. 7.

Kottler et al., "X-ray phase contrast imaging of soft tissue specimens," IEEE Nuclear Science Symposium Conference Record, Oct. 23-29, 2011, pp. 4437-4440.

Poletto et al., "A system for high-resolution X-ray phase-contrast imaging and tomography of biological specimens," Proceedings of SPIE, Sep. 3, 2008, pp. 70781P-1-70781P-10, vol. 7078.

Pfeiffer et al., "Phase retrieval and differential phase-contrast imaging with low-brilliance X-ray sources," Nature Physics, Apr. 2006, pp. 258-261, vol. 2.

Olivo et al., "Amplification of the phase contrast signal at very high x-ray energies," Optics Letters, Mar. 1, 2012, pp. 915-917, vol. 37, No. 5.

Yashiro et al., "Distribution of unresolvable anisotropic microstructures revealed in visibility-contrast images using x-ray Talbot interferometry," Physical Review B, Sep. 19, 2011, pp. 094106.

De Caro et al., "A theoretical study on phase-contrast mammography with Thomson-scattering x-ray sources," Medical Physics, Oct. 2009, pp. 4644-4653, vol. 36, No. 10.

Kottler et al., "Dual energy phase contrast x-ray imaging with Talbot-Lau interferometer," Journal of Applied Physics, Dec. 7, 2010, pp. 114906.

Engelhardt et al., "High-resolution differential phase contrast imaging using a magnifying projection geometry with a microfocus x-ray source," Applied Physics Letters, May 30, 2007, pp. 224101.

* cited by examiner

IMAGING SYSTEM

CROSS-REFERENCE TO RELATED APPLICATION

This application claims the priority benefits of U.S. provisional application Ser. No. 61/739,017, filed on Dec. 19, 2012 and Taiwan application serial no. 102142336, filed on Nov. 20, 2013. The entirety of each of the above-mentioned patent applications is hereby incorporated by reference herein and made a part of this specification.

FIELD OF THE DISCLOSURE

The disclosure relates to an imaging system, and particularly relates to an X-ray phase contrast imaging system.

DESCRIPTION OF RELATED ART

X-ray (i.e., X-light) medical imaging is a non-invasive method for checking the structure inside a human body and it can be quickly aware of the anatomy information of a subject (such as shape structures of bones, organs and soft tissues) without performing anatomy practice or tissue sectioning. Therefore, X-ray medical imaging result has served as one of the bases of medical diagnosis.

The conventional X-ray imaging technology uses X-ray with higher-frequency energy range, which has excellent distinguishable capability to recognize bones from soft tissue so as to be often used for bone radiography. However, because the composition differences of soft tissues at various parts of the body are not significant, the image differences within the X-ray energy range of bone radiography caused by the composition differences between the soft tissues are not significant as well. As a result, the soft tissue imaging result is not easily distinguished and is difficult to serve for medical diagnosis on soft tissues.

In recent years however, along with digitizing the X-ray images, the soft tissue radiography through the X-ray becomes feasible already. It should be noted that the attenuations of X-ray with different energy ranges after penetrating through bones and soft tissue are different. Based on the principle, a dual-energy X-ray system with two different energy ranges are used to respectively take photograph on a body position and obtain the X-ray images, followed by a signal processing, the images for the soft tissue and the hard tissue (or the images of contrast agent or implant) can be distinguished from each other. By using the X-ray with different energy ranges, the attenuation difference on the bone is significant, but it is not significant on the soft tissue. After performing the successive image processing of the dual-energy X-ray system, the recognisability for soft tissues in the image can be advanced, which facilitates to aid medical diagnosis. The X-ray phase contrast imaging technology is another technology which enhances the imaging of low atomic number materials or soft tissues, wherein high-coherence light sources or light gratings are employed so that the phase information of the light generated after the photons of X-ray pass through the object may improve the contrast effect of the image. The contrast ratio of the low atomic number material image can be improved and thus it is helpful in clinical or industrial fields. The imaging technology with the combination of dual-energy and phase contrast not only can perform nondestructive detecting, but also can increase the contrast ratio of the low atomic number material image, and thus it further can analyze composition of materials. Nevertheless, that needs two optical systems in order to individually receive different X-ray energies twice, and it may increase the fabricating cost of the apparatus. Additionally, for the person who is irradiated the X-ray twice or more, it is not only bad for health, the image difference may also occur due to the person's movement during the two-time irradiation. Accordingly, the image difference may affect the following image processing and blur or residual image may be generated, and the medical diagnosis may further be affected.

SUMMARY OF THE DISCLOSURE

The disclosure provides an imaging system adapted to be used for material discrimination of an object.

The imaging system of the disclosure includes an X-ray source and a sensor. The X-ray source generates a multienergy polychromatic X-ray, wherein there is an integral multiple relationship between multienergy bands of the X-ray. The object is adapted to be disposed between the X-ray source and the sensor. Herein the X-ray is transmitted toward and detected by the sensor through irradiating the object, and multienergy bands of the sensor correspond to the multienergy bands of the X-ray.

In light of the above, in the imaging system described in the embodiment, the X-ray source which provides a multienergy polychromatic X-ray is disposed and the multienergy bands of the sensor correspond to the multienergy bands of the X-ray. In such configuration, through phase contrast, the imaging system can achieve the effect of simultaneously resolving the phase contrast of multienergy bands, by only using a fixed imaging distance and optical element and performing a single irradiation. Therefore, the image contrast of the phase-sensitive object can be enhanced and material discrimination of the object is also facilitated.

To make the above features of the disclosure more comprehensible, several embodiments accompanied with drawings are described in detail as follows.

DESCRIPTION OF EMBODIMENTS

Figure 1:
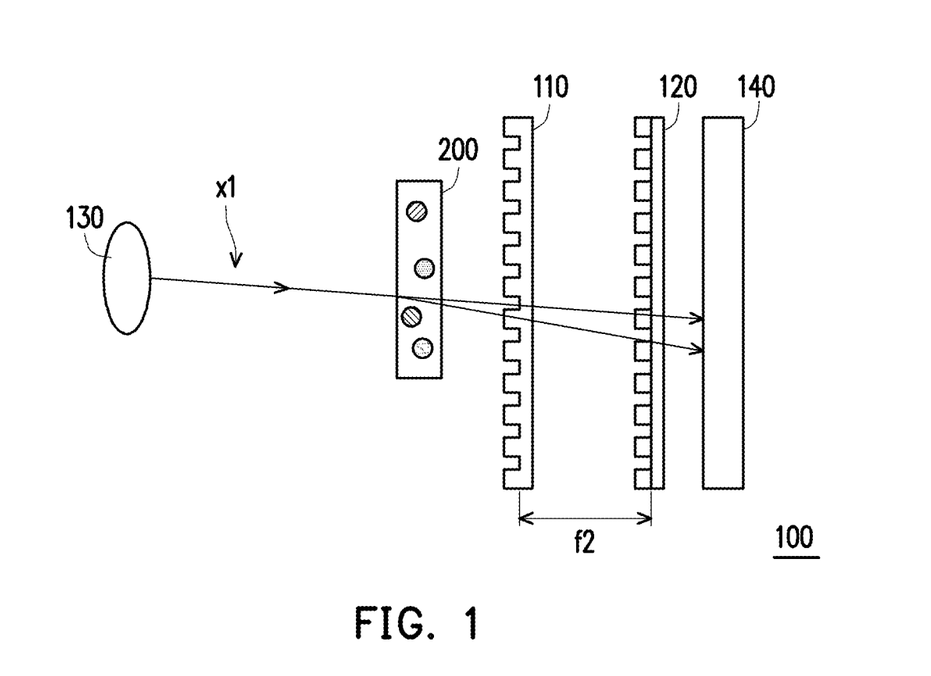
FIG. 1 is a schematic view of an X-ray imaging system according to an exemplary embodiment of the disclosure.
Figure 2:
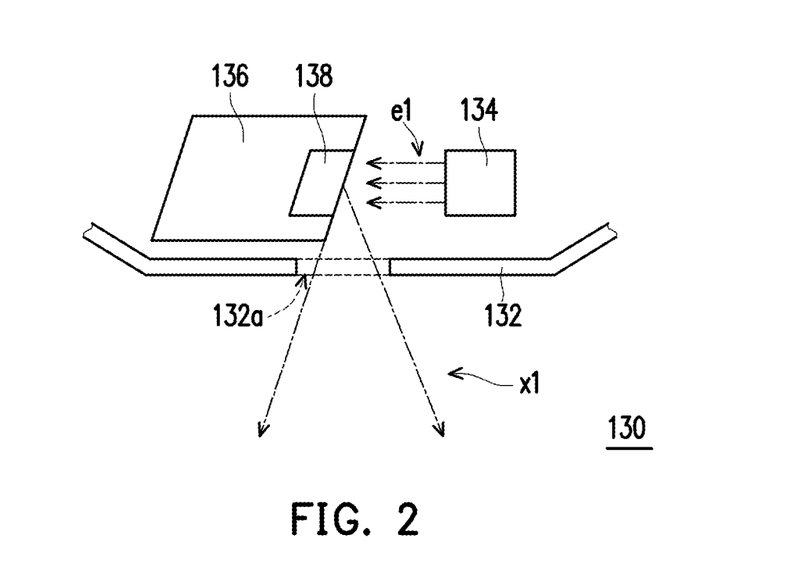
FIG. 2 is a schematic view of the X-ray source of the imaging system of FIG. 1.
Figure 3:
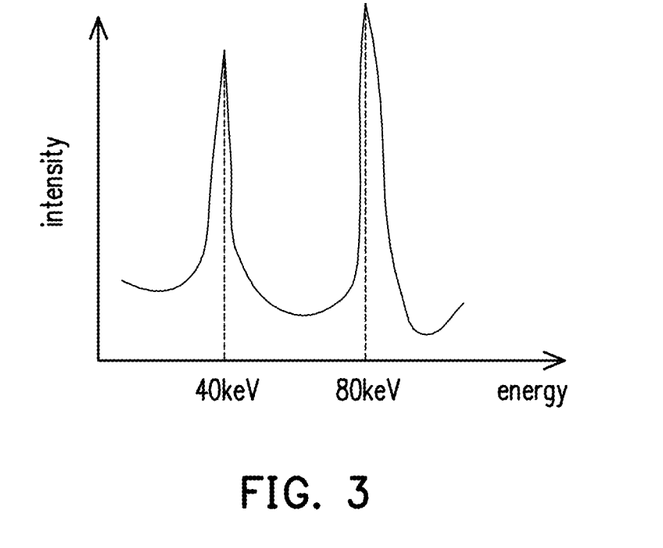
FIG. 3 is the X-ray spectrogram at the X-ray source of the X-ray imaging system of FIG. 1.
Figure 4:
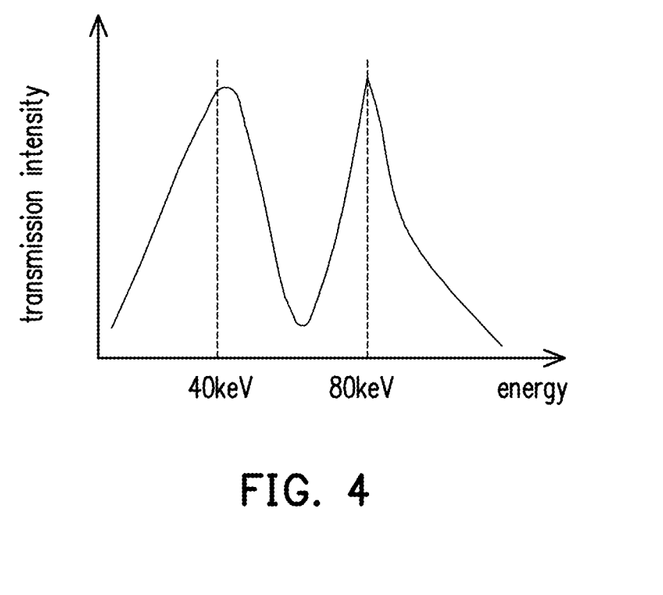
FIG. 4 is the X-ray spectrogram detected by the sensor of the X-ray imaging system of FIG. 1.

FIG. 1 is a schematic view of an X-ray imaging system according to an exemplary embodiment of the disclosure. FIG. 2 is a schematic view of the X-ray source of the imaging system of FIG. 1, and only parts of components are shown for equivalent representing. FIG. 3 is the X-ray spectrogram at the X-ray source of the X-ray imaging system of FIG. 1. FIG. 4 is the X-ray spectrogram detected by the sensor of the X-ray imaging system of FIG. 1. Referring to FIG. 1 through FIG. 4 together, in the embodiment, the imaging system 100 includes an X-ray source 130, a first light grating 110, a second light grating 120 and a sensor 140, wherein an object 200 is adapted to be disposed between the X-ray source 130 and the sensor 140, the first light grating 110 is disposed between the object 200 and the sensor 140, and the second light grating 120 is disposed between the first light grating 110 and the sensor 140. The X-ray source 130 is a characteristic radiation and used for generating multienergy polychromatic X-ray x1, and the X-ray passes through the object 200, the first light grating 110 and the second grating 120, and is transmitted toward and detected by the sensor 140. In the figure, x1 is merely shown for representing X-ray.

Accordingly, the imaging system 100 has the characteristics of the conventional dual-energy X-ray source which can be used for distinguishing between different atomic number materials and solving the current problem that using absorption method but unable to distinguishing between low atomic number materials or materials the atomic numbers thereof are close. The imaging system 100 can be used for distinguishing between soft tissues and hard tissues in the medical imaging application. In addition, by using the optical system formed by the light gratings 110, 120, the imaging system 100 of the embodiment can enhance the image contrast ratio of the material after imaged by using the phase contrast method, so as to analyze the material composition of the object 200. The X-ray x1 of the embodiment is multienergy polychromatic X-ray, and the multienergy bands of the X-ray correspond to the multienergy bands of the sensor 140 which can resolve energy bands. Therefore, the configuration of components of the phase contrast system of the conventional dual-energy X-ray and the imaging process can be simplified, namely, only one fixed optical system (i.e., the optical design is constructed according to one of the wavelengths, so that optical characteristics and a fixed imaging distance of the light gratings 110, 120 are determined thereby) and a single irradiation are used, in order that the material composition of the object 200 can be analyzed. Thus, consideration of inconvenience and unsafety due to different optical gratings (for corresponding to wavelengths with different energies) and imaging by several-time exposures which are necessary in the conventional method can be effectively avoided.

Further, the sensor 140 can resolve multienergy bands, and the multienergy bands correspond to multienergy bands of the X-ray x1, respectively. As shown in FIG. 3 and FIG. 4, two energy bands $E_1$ and $E_2$ are selected out of the multiwavelength of the X-ray in the embodiment, for example, the energy bands $E_1$ and $E_2$ are 40keV and 80key, respectively. In addition, the full width at half maximum (FWHM) of each energy band is less than or equal to 30%, and there exists an integral multiple relationship between the multienergy bands, wherein $E_2=n*E_1$ (n is an integer), i.e., the larger energy central wavelength is correspondingly an integral multiple of the smaller energy central wavelength. In the embodiment, $E_1$ and $E_2$ are 40keV and 80 keV, and n is 2. Correspondingly, the energy bands which can be resolved by the sensor 140 are distributed corresponding to the energy bands of the X-ray source 130, and also are the same to the energy bands, $E_1$ (40keV) and $E_2$ (80 keV) (namely, at the corresponding spectrum of the X-ray source 130, there is also an integral multiple relationship). As such, all of the multienergy bands of the X-ray x1 can be detected by the sensor 140, and thus the desired phase contrast imaging effect can be achieved by merely using one optical design and a single irradiation imaging. Herein only two energy bands $E_1$ keV and $E_2$ keV are described in this embodiment, in other embodiments other energy bands of the X-ray x1 can be selected as long as comply with the fact that there is an integral multiple relationship between the larger energy wavelength and the smallest energy wavelength, for example, 10 keV, 20 keV, and 30 keV.

Figure 5:
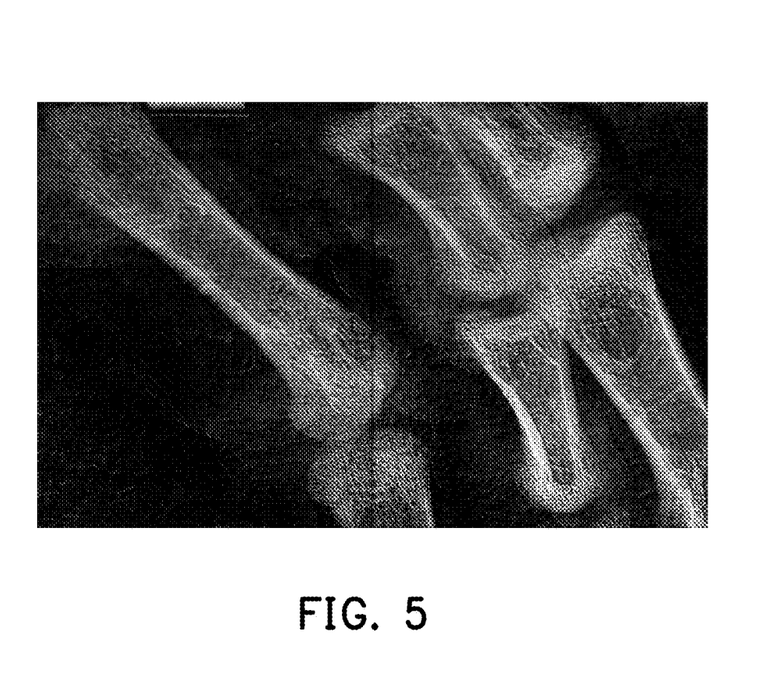
FIG. 5 and FIG. 6 are phase contrast images formed by different energy bands of the X-ray.
Figure 6:
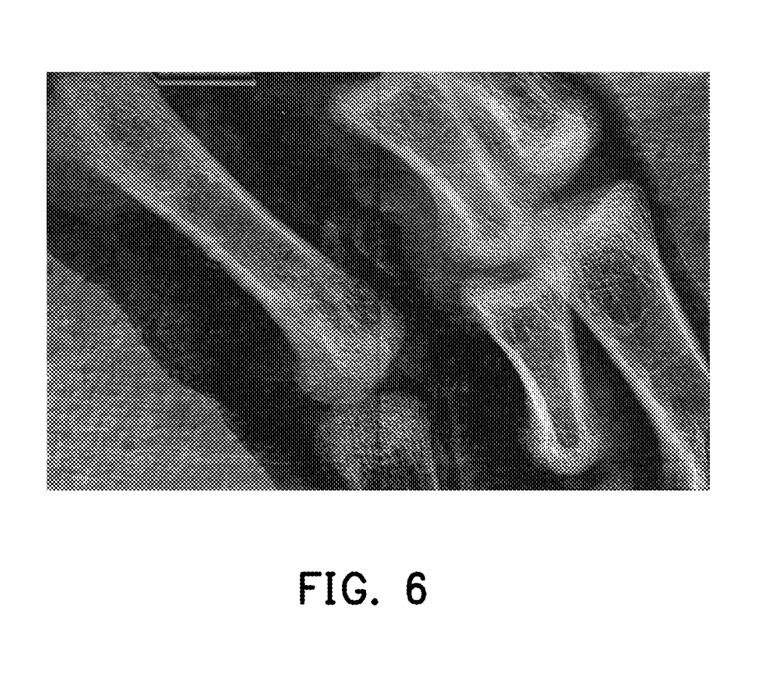

FIG. 5 and FIG. 6 are phase contrast images formed by different energy bands of the X-ray. Herein bones, muscles and soft tissues therebetween are referred to as the object, wherein the image in FIG. 5 is generated by image processing after imaging by using the energy bands 40 keV and 80 keV, and the image in FIG. 6 is generated by image processing after imaging by using the energy bands 40 keV and 140 keV. It is clearly seen in the images that the effect of the distinguishing between the soft and hard tissues when there is an integral multiple relationship between the energy bands of the X-ray is more significant than that when there is no integral multiple relationship therebetween (i.e., FIG. 6 is not such distinct that the soft tissue and the bone are separated).

In other words, in the optical design of the embodiment, the first light grating 110, the second light grating 120, and the optical characteristics thereof are related to the wavelength of the light source. In the embodiment, the pitch of the first light grating 110 is p1, the central wavelength of the X-ray is λ, the distance between the first light grating 110 and the second light grating 120 is f2, therefore, $f2=n*(p1)^2/\lambda$ (n is an integer). Namely, in the condition of the energy wavelengths of the X-ray x1 being in an integral multiple relationship, the imaging distance f2 does not need to vary with the wavelength of the X-ray x1, and thus a constructive interference image can be generated by performing a single irradiation of the X-ray x1.

Referring to FIG. 2, in the embodiment, the X-ray source 130 includes a body 132, an electron gun 134, a clamping member 136 and a target 138. The body 132 has an opening 132a, the electron gun 134 is adapted to emit an electron beam e1, the target 138 is a composite material target which is disposed in the body 132 and near to the opening 132a, and the target 138 is fixed onto the clamping member 136 so as to rotate with the clamping member 136 or be fixed in a position. Accordingly, the electron beam e1 emitted from the electron gun 134 impinges onto the target 138, so that the X-ray x1 irradiates out through the opening 132a of the body 132. In this embodiment, a reflective X-ray source and a target which is fixed are representatively described. In other embodiments, the clamping member 136 and the target 138 can also be rotatable, wherein the rotatable target may facilitate dissipating the high temperature generated when the electron beam e1 impinging onto the target 138. In another exemplary embodiment which is not shown in figure, the X-ray source can also be a transmission X-ray, wherein the opening of the body is located behind the target and disposed in a straight line with the electron gun. It is described in the embodiment illustrated in FIG. 17.

It should be noted that, a composite material target is used in the embodiment so that a multienergy polychromatic X-ray can be generated. The composite material target includes at least two different materials. In order to form multienergy polychromatic X-ray having an integral multiple relationship therebetween, the target materials has to be selected and collocated. Table 1 is the relationship of the target materials and the energy bands of the X-ray generated after the electron impinging onto the materials.

TABLE 1

| Target material | X-ray energy band (keV) |
|---|---|
| Scandium (Sc) | 4.5 |
| Copper (Cu) | 9 |
| Gallium (Ga) | 10 |
| Molybdenum (Mo) | 20 |
| Antimony (Sb) | 30 |
| Cerium (Ce) | 40 |
| Gadolinium (Gd) | 50 |
| Ytterbium (Yb) | 60 |
| Tungsten (W) | 70 |
| Gold (Au) | 80 |
| Bismuth (Bi) | 90 |
| Francium (Fr) | 100 |

It can be known from Table 1 that, in one embodiment, if an X-ray with two times in the relationship is to be generated, combinations of scandium and copper, gallium and molybdenum, molybdenum and cerium, and so on, can be selected. If an X-ray with three or more energy bands is to be generated, three different target materials such as a combination of gallium, molybdenum and antimony, or a combination of gallium, molybdenum and cerium, and so on can be selected. It should be noted that, if three or more target materials are selected, it is only required that the smallest energy band of the X-ray generated by the selected target material being in an integral multiple relationship with the other two larger energy bands of the X-ray, and it is unnecessary that every two energy bands of the X-ray generated by the selected target materials are in an integral multiple relationship. In brief, the materials are selected in order that an integral multiple relation exists between the multienergy bands of the x-ray which is generated by the electron beam impinging onto the target.

Figure 7:
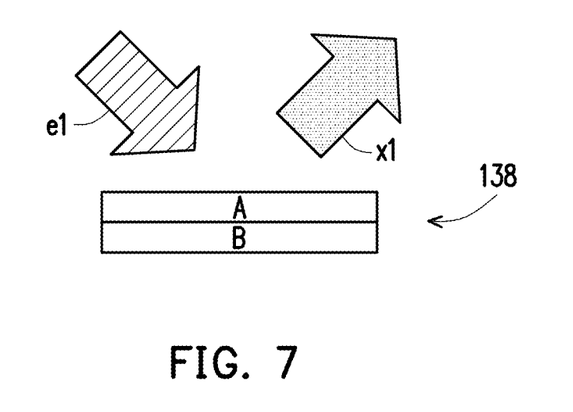
FIG. 7 and FIG. 8 are side views of targets of different embodiments.
Figure 8:
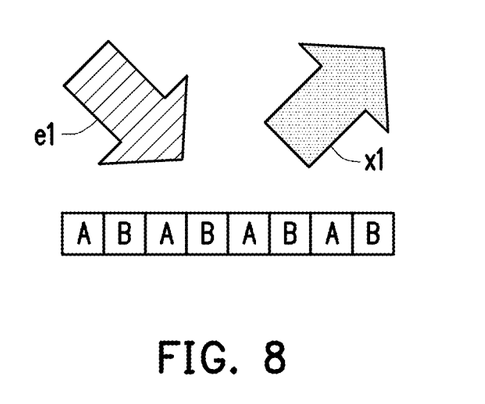

Herein FIG. 7 and FIG. 8 are side views showing the targets in different embodiments, wherein as shown in FIG. 7, the target is formed by a stacked structure or an embedded structure of different materials A and B, for example, formed by multi-layer coating method. In addition, the target of FIG. 8 is formed by different materials A and B that are alternately combined. Herein the stacking method of the materials is not limited in the disclosure, and the different materials may be vertically stacked or horizontally stacked.

Figure 9:
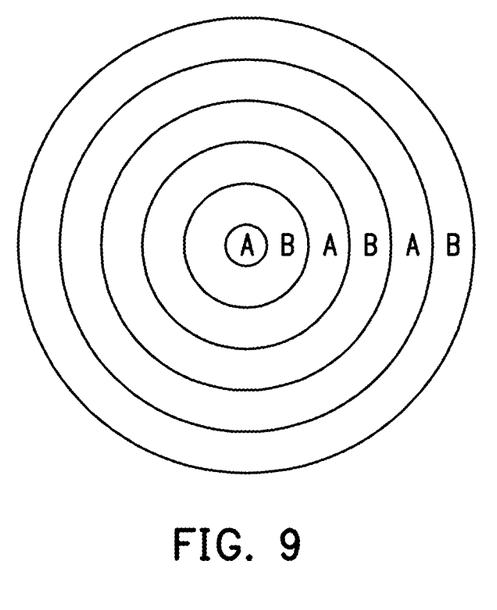
FIG. 9, FIG. 10 and FIG. 11 are top views of targets of different embodiments.
Figure 10:
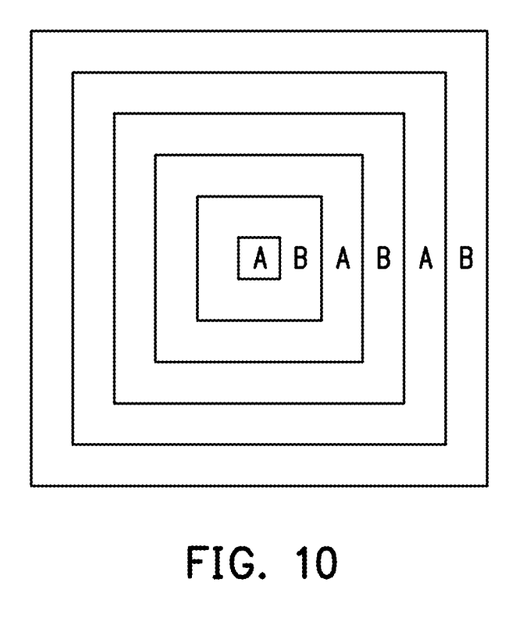
Figure 11:
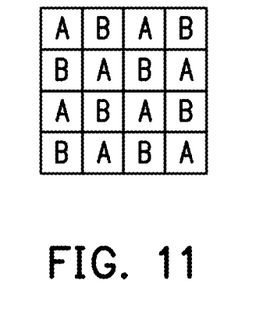

Additionally, FIG. 9, FIG. 10 and FIG. 11 are top views of targets of different embodiments. As shown in FIG. 9, FIG. 10 and FIG. 11, the targets that the materials are alternately combined are illustrated in FIG. 9 and FIG. 10, wherein the materials A and B having different contours are concentrically arranged, and as shown in FIG. 11, the different materials A and B are arranged in arrays. Accordingly, the designer may appropriately dispose the composite material target according to desired testing condition of the material.

Figure 12:
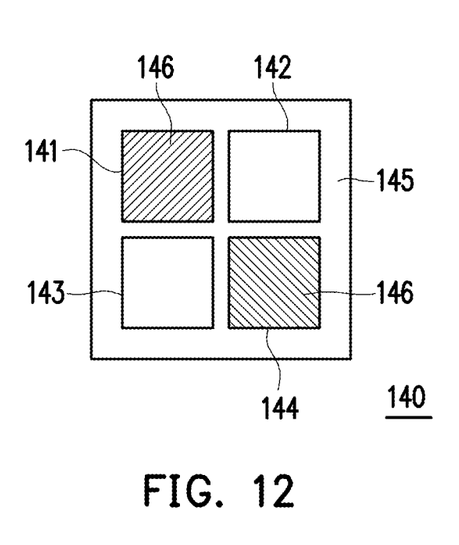
FIG. 12 is a partially magnified view illustrating the sensor of the imaging system of FIG. 1.
Figure 13:
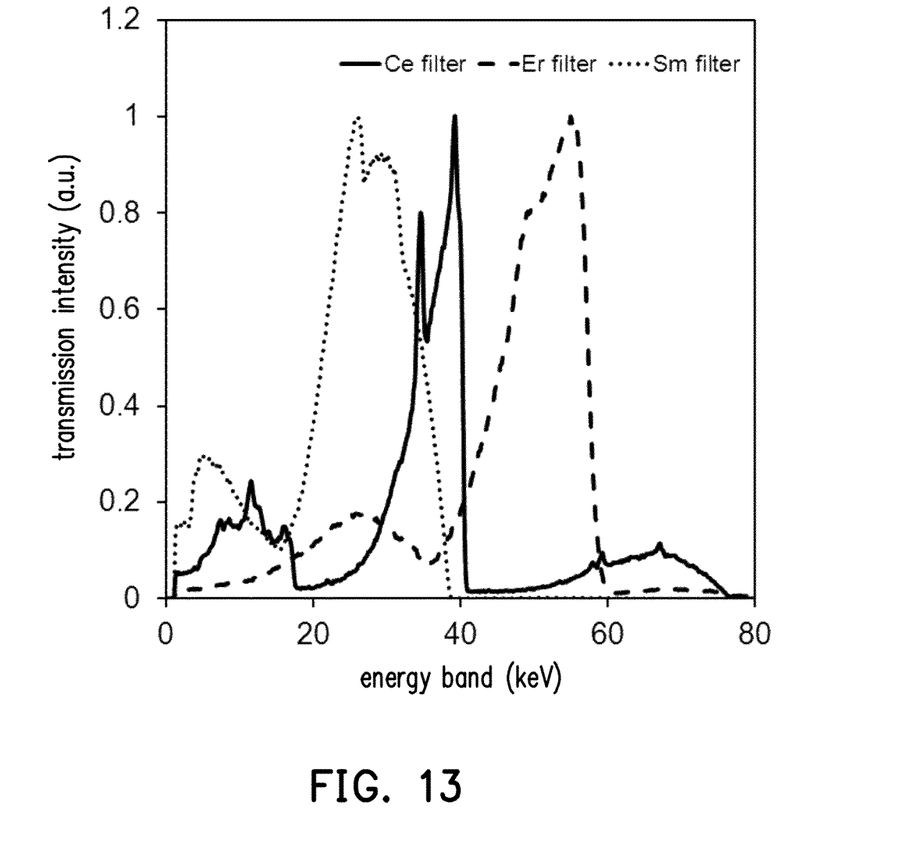
FIG. 13 is a spectrum diagram of different materials corresponding to the change of irradiation intensity of each multienergy band of the X-ray.

FIG. 12 is a partially magnified view illustrating the sensor of the imaging system of FIG. 1. The sensor 140 is used for directly detecting and converting the X-ray x1 which passed through the object 200 and the optical system. Each pixel 145 of the sensor 140 has a plurality of sub-pixels 141, 142, 143, 144, and in the embodiment, a single pixel 145 may be divided into four sub-pixels. However it is not limited thereto. In the sub-pixels 141, 142, 143, 144, at least one sub-pixel is provided with a filtering material 146 (as shown in FIG. 12, the sub-pixels 141 and 144 are provided with filtering materials 146), wherein the energy band of the filtering material 138 corresponds to at least one energy band of the multienergy band of the X-ray x1. In more detailed, taking the X-ray x1 having two energy bands as an example, the sub-pixels 142 and 143 which are not provided with a filtering material may be capable of receiving the two energy bands of the X-ray x1; and as for the sub-pixels 141 and 144 which are provided with a filtering material 146, when the plurality energy bands of the X-ray x1 enter the sub-pixels 141 and 144, one of the energy bands is absorbed by the filtering material 146, namely, only the other energy band of the X-ray x1 is received by the sub-pixels 141 and 144. Therefore, the sub-pixels 141 and 144 may detect and generate an image signal having a single energy band, whereas the sub-pixels 142 and 143 may detect and generate an image signal having two energy bands. In the signal analyzing process, by subtracting between the two-energy image signal generated by the sub-pixels 142 and 143 and the single energy image signal generated by the sub-pixels 141 and 144, the image signal of the other energy band can be obtained. Accordingly, effect of multienergy band being resolved can be achieved. In other embodiments, different filtering materials 146 may be disposed in all of the sub-pixels 141, 142, 143, 144, in order that filtering process can be done to every energy band of the multienergy polychromatic X-ray x1. It should be noted that the selecting of the filtering material 146 and the material of target 138 are matched each other, i.e., it is required that the filtering material 146 is required to be capable to absorb at least one of the energy bands of the X-ray x1 generated by the composite target 138. The following describe an example: FIG. 13 is a spectrum diagram of different materials corresponding to the change of irradiation intensity of each multienergy band of the X-ray. As shown in FIG. 13, samarium (Sm) has a good irradiation intensity at 25 to 35 keV of the X-ray energy band, thus if antimony (Sb) is selected to be the target material, samarium (Sm) may be selected to be the filtering material 146. Cerium (Ce) has a good irradiation intensity at 30 to 40 keV of the X-ray energy band, thus if antimony (Sb) or cerium (Ce) is selected to be the target material, cerium (Ce) may be selected to be the filtering material. Erbium (Er) has a good irradiation intensity at 50 to 60 keV of the X-ray energy band, thus if gadolinium (Gd) or ytterbium (Yb) is selected to be the target material, erbium (Er) may be selected to be the filtering material.

In addition, in another embodiment which is not shown in figures, the sensor 140 may also be a photon counting detector which may also achieve the effect of resolving of multienergy band of the X-ray.

Figure 14:
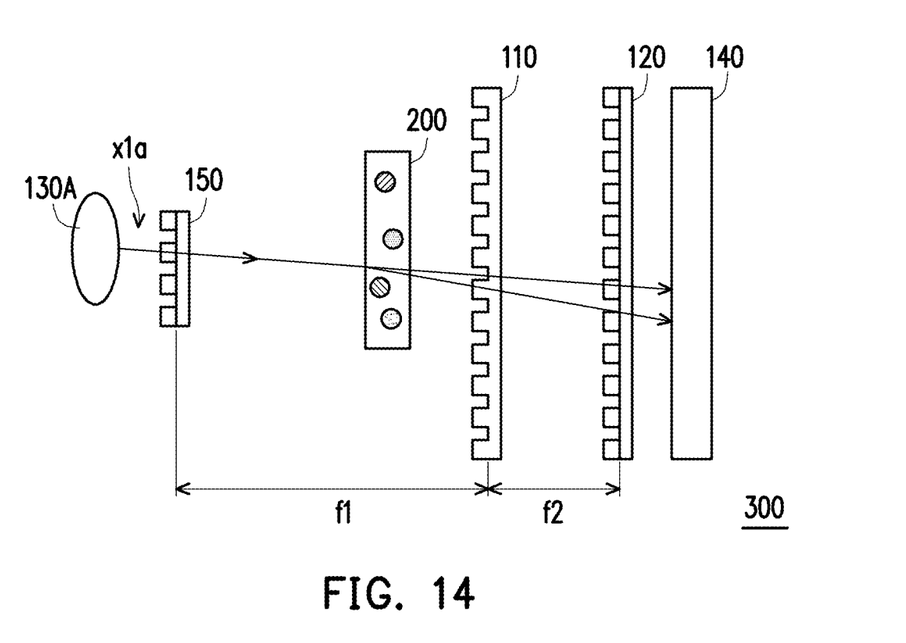
FIG. 14 is a schematic view of an imaging system according to another exemplary embodiment of the disclosure.

FIG. 14 is a schematic view of an imaging system according to another exemplary embodiment of the disclosure. The difference between this embodiment and the abovementioned embodiment is that, the X-ray source 130A is used for mainly generating bremsstrahlung, for example, the target is made of tungsten (W). Accordingly, the imaging system 300 further includes a third light grating 150, wherein the third light grating 150 is a zero-order grating, for example, a silicon (Si) grating disposed between the X-ray source 130A and the object 200. Herein the third light grating 150 is used for narrowing the bandwidth of the X-ray x1a generated by the X-ray source 130A. In addition, as for the optical design, the pitch of the second light grating 120 is p2, the pitch of the third light grating 150 is p0, then $p0=p2/f2=n*X*p2/(p1)^2$. As mentioned above, in the condition of the energy central wavelengths of the X-ray x1a being in an integral multiple relationship, the imaging distances f1, f2 do not need to vary with the wavelength of the X-ray, and thus a constructive interference image can be generated by performing a single irradiation of the X-ray x1a.

In another embodiment which is not shown in figures, in order to achieve the narrowing down effect of the energy band as abovementioned, a metal coating layer can be coated at the opening of the X-ray source so as to achieve an equivalent effect of the third light grating 150. In other words, through the metal coating layer coated at the opening of the X-ray source, the metal coating layer may be used as a filtering material.

Figure 15:
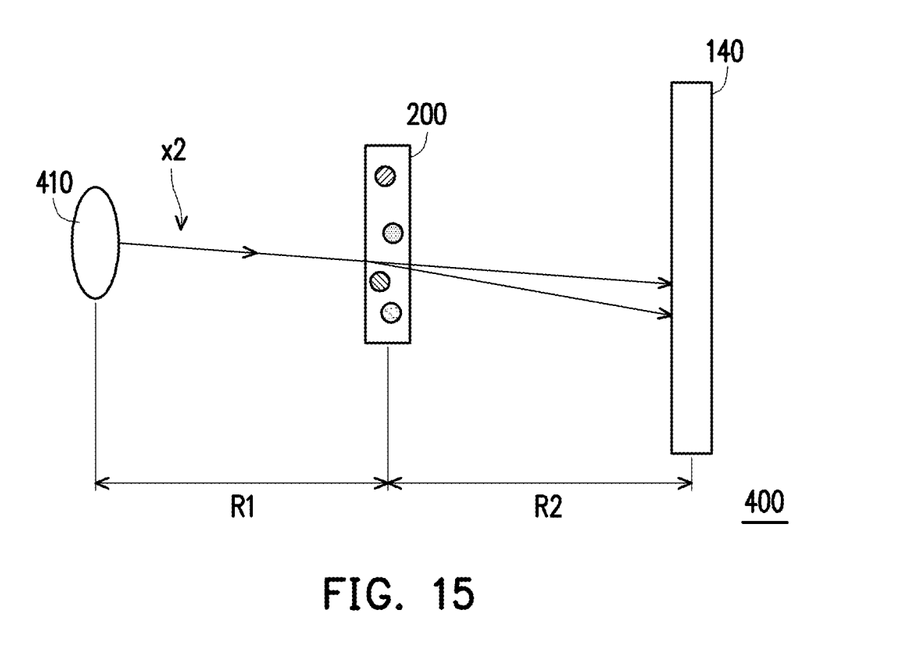
FIG. 15 is a schematic view of an imaging system according to another exemplary embodiment of the disclosure.
Figure 16:
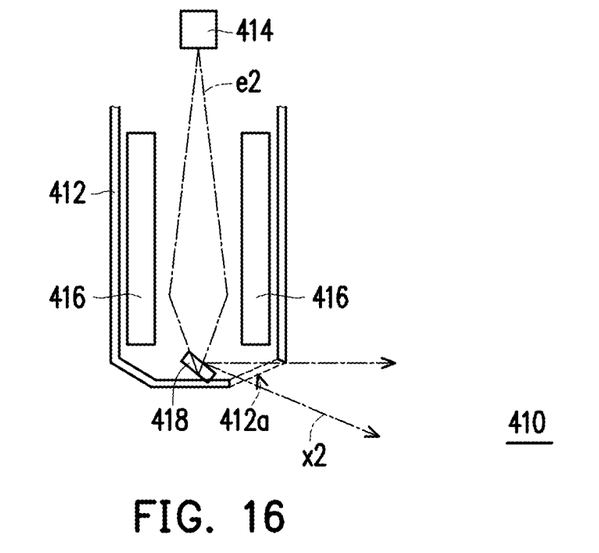
FIG. 16 is a schematic view of the X-ray source of the imaging system of FIG. 14.

FIG. 15 is a schematic view of an imaging system according to another exemplary embodiment of the disclosure. FIG. 16 is a schematic view of the X-ray source of the imaging system of FIG. 15, and only parts of components are shown for description. Referring to FIG. 15 and FIG. 16, the difference between this embodiment and the abovementioned embodiment is that, the X-ray source 410 of the imaging system 400 is a microfocus X-ray source, wherein a spot size thereof is smaller than 50 μm, thus the light gratings disposed in the abovementioned embodiments can be omitted, and it still has the optical characteristics described as followed:

The distance between the X-ray source 410 and the object 200 is R1, the distance between the object 200 and the sensor 140 is R2, then $L_{coh} = \lambda R1/s$, $L_{shear} = \lambda R2^*|u|/M$; and $L_{shear}/L_{coh} \ll 1$; wherein $M = (R1+R2)/R1$, $\lambda$ is the wavelength of the X-ray, s is the spot size of the X-ray generated by the X-ray source 410, $L_{coh}$ is the spatial coherence length of the X-ray, $L_{shear}$ is the phase-space shearing length, and u is the structural spatial frequency of the composition of the object. As mentioned above, in the condition of the energy central wavelengths of the X-ray of the embodiment being in an integral multiple relationship, the imaging distances R1, R2 only need to adjust the central wavelength of the smallest energy band and do not need to vary with the wavelength of the X-ray, and thus a constructive interference image can be generated by performing a single irradiation of the X-ray. Similarly, the sensor 140 is also required to resolve the multienergy band of the corresponding X-ray and be in an integral multiple relationship, and it is not repeated herein.

Figure 17:
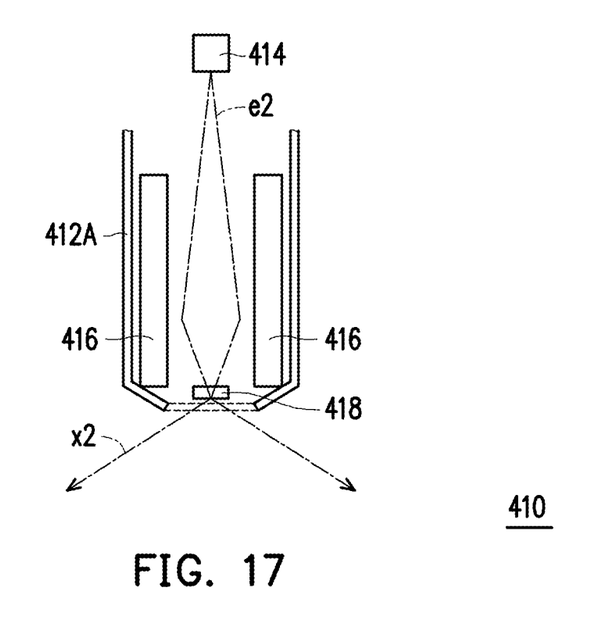
FIG. 17 is a schematic view of an X-ray source of another exemplary embodiment of the disclosure.

Referring to FIG. 16, in order to form the microfocus X-ray, the X-ray source 410 of the embodiment includes a body 412, an electron gun 414, an electromagnetic lens 416 and a target 418, wherein the body 412 has an opening 412*a*, and the electron gun 414 is disposed in the body 412 and opposite to the opening 412*a*. The electromagnetic lens 416 is disposed in the body 412 and located between the electron gun 414 and the opening 412*a*. The target 418 is a composite material target which is disposed in the body 412 and near the opening 412*a*. Accordingly, the electron beam e2 emitted from the electron gun 414, focused by the electromagnetic lens 416 and then impinges onto the target 418, so that the X-ray x2 irradiates out through the opening 412A of the body 412. In addition, FIG. 17 is a schematic view of an X-ray source of another exemplary embodiment of the disclosure, wherein merely the reflective X-ray source of FIG. 16 is replaced by a transmission X-ray source in FIG. 17, the opening of the body 412A is located behind the target 418 and disposed in a straight line with the electron gun 414, the abovementioned effect may also be achieved.

In light of the foregoing, in the embodiments of the disclosure, the imaging system is provided with an X-ray source and the X-ray source provides a multienergy polychromatic X-ray, wherein the multienergy band of the X-ray are in an integral multiple relationship and the multienergy band of the sensor correspond to the multienergy bands of the X-ray. In such configuration, it is merely required to design the optical system corresponding to one of the energy wavelength, then the imaging system can achieve the effect of simultaneously resolving the phase constrast of multienergy bands, by only performing a single irradiation. Therefore, the image contrast of the phase-sensitive object can be enhanced and material discrimination of the object is also facilitated.

Although the disclosure has been described with reference to the above embodiments, it will be apparent to one of ordinary skill in the art that modifications to the described embodiments may be made without departing from the spirit of the disclosure. Accordingly, the scope of the disclosure will be defined by the attached claims and not by the above detailed descriptions.

What is claimed is:

1. An imaging system, adapted to be used for material discrimination of an object, the imaging system comprising:
    an X-ray source, generating a multienergy polychromatic X-ray, wherein there is an integral multiple relationship between multienergy bands of the X-ray; and
    a sensor, the object disposed between the X-ray source and the sensor, wherein the X-ray is transmitted toward and detected by the sensor through irradiating the object, and multienergy bands of the sensor correspond to the multienergy bands of the X-ray.

2. The imaging system as claimed in claim 1, wherein a full width at half maximum of each multienergy band of the X-ray is less than or equal to 30%.

3. The imaging system as claimed in claim 1, wherein the X-ray source comprises:
    a body, having an opening;
    an electron gun, adapted to emit an electron beam; and
    a target, being a composite material target, disposed in the body and near to the opening, wherein the electron beam emitted by the electron gun impinges onto the target, so that the X-ray irradiates out through the opening of the body,
    wherein the target comprises at least two different materials, and the materials are selected in order that an integral multiple relation exists between the multienergy bands of the X-ray which is generated by the electron beam impinging onto the target.

4. The imaging system as claimed in claim 3, wherein the electron gun is disposed in the body and opposite to the opening, and the X-ray source further comprises an electromagnetic lens disposed in the body and located between the electron gun and the opening to focus the electron beam emitted by the electron gun.

5. The imaging system as claimed in claim 4, wherein the opening of the body is located behind the target and disposed in a straight line with the electron gun.

6. The imaging system as claimed in claim 3, wherein the materials are formed stacked with each other or alternately combined.

7. The imaging system as claimed in claim 1, wherein the X-ray source comprises a microfocus source.

8. The imaging system as claimed in claim 7, wherein a spot size of the X-ray source is smaller than 50 μm.

9. The imaging system as claimed in claim 1, wherein each pixel of the sensor has a plurality of sub-pixels, and at least one of the sub-pixels has a filtering material, and an energy band of the filtering material corresponds to at least one energy band of the multienergy bands of the X-ray.

10. The imaging system as claimed in claim 1, wherein the sensor comprises a photon counting detector.

11. The imaging system as claimed in claim 1, further comprising:
    a first light grating, disposed between the object and the sensor; and
    a second light grating, disposed between the first light grating and the sensor, wherein the X-ray sequentially passes through the object, the first light grating and the second grating, and is transmitted toward and detected by the sensor.

12. The imaging system as claimed in claim 11, wherein the X-ray is a bremstrahlung X-ray, and the imaging system further comprises:
a third light grating, disposed between the X-ray source and the object, wherein the third light grating is used for narrowing a bandwidth of the multienergy band generated by the X-ray source.

* * * * *